US010590477B2

(12) United States Patent
Koh et al.

(10) Patent No.: US 10,590,477 B2
(45) Date of Patent: Mar. 17, 2020

(54) METHOD AND APPARATUS FOR PURIFYING NUCLEIC ACIDS AND PERFORMING POLYMERASE CHAIN REACTION ASSAYS USING AN IMMISCIBLE FLUID

(71) Applicant: National Technology & Engineering Solutions of Sandia, LLC, Albuquerque, NM (US)

(72) Inventors: Chung-Yan Koh, Dublin, CA (US); Yooli Kim Light, Pleasanton, CA (US); Matthew Ernest Piccini, Belmont, CA (US); Anup K. Singh, Danville, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 213 days.

(21) Appl. No.: 15/717,524

(22) Filed: Sep. 27, 2017

(65) Prior Publication Data
US 2018/0037932 A1 Feb. 8, 2018

Related U.S. Application Data

(62) Division of application No. 14/090,040, filed on Nov. 26, 2013, now Pat. No. 9,803,238.

(51) Int. Cl.
C12Q 1/68 (2018.01)
C12Q 1/686 (2018.01)
(Continued)

(52) U.S. Cl.
CPC ........ *C12Q 1/686* (2013.01); *B01L 3/502761* (2013.01); *B01L 7/52* (2013.01);
(Continued)

(58) Field of Classification Search
None
See application file for complete search history.

(56) References Cited

U.S. PATENT DOCUMENTS 3,555,284 A 1/1971 Anderson
3,744,974 A 7/1973 Maddox
(Continued)

FOREIGN PATENT DOCUMENTS

WO WO-2008/143578 11/2008
WO WO-2009/098237 8/2009

OTHER PUBLICATIONS

Pipper et al. (Angew Chem Int Ed, 2008, 47:3900-3904) (Year: 2008).*

(Continued)

*Primary Examiner* — Stephanie K Mummert
(74) *Attorney, Agent, or Firm* — Helen S. Baca

(57) ABSTRACT

Embodiments of the present invention are directed toward devices, systems, and methods for purifying nucleic acids to conduct polymerase chain reaction (PCR) assays. In one example, a method includes generating complexes of silica beads and nucleic acids in a lysis buffer, transporting the complexes through an immiscible fluid to remove interfering compounds from the complexes, further transporting the complexes into a density medium containing components required for PCR where the nucleic acids disassociate from the silica beads, and thermocycling the contents of the density medium to achieve PCR. Signal may be detected from labeling agents in the components required for PCR.

20 Claims, 8 Drawing Sheets

(51) Int. Cl.
  *B01L 3/00* (2006.01)
  *B01L 7/00* (2006.01)
(52) U.S. Cl.
  CPC .......... *B01L 2200/0668* (2013.01); *B01L 2300/0803* (2013.01); *B01L 2300/087* (2013.01); *B01L 2300/1827* (2013.01); *B01L 2400/0409* (2013.01)

(56) References Cited

U.S. PATENT DOCUMENTS

| | | |
|---|---|---|
| 4,125,375 A | 11/1978 | Hunter |
| 4,156,570 A | 5/1979 | Wardlaw |
| 4,554,071 A | 11/1985 | Ruijten et al. |
| 4,656,143 A | 4/1987 | Baker et al. |
| 4,683,579 A | 7/1987 | Wardlaw |
| 4,844,818 A | 7/1989 | Smith |
| 5,279,936 A | 1/1994 | Vorpahl |
| 5,635,362 A | 6/1997 | Levine et al. |
| 5,639,428 A * | 6/1997 | Cottingham .......... B01L 3/502 422/105 |
| 5,705,628 A | 1/1998 | Hawkins |
| 5,882,903 A | 3/1999 | Andrevski et al. |
| 5,892,577 A | 4/1999 | Gordon |
| 6,153,148 A | 11/2000 | Thomas |
| 6,319,469 B1 | 11/2001 | Mian et al. |
| 6,503,722 B1 | 1/2003 | Valkirs |
| 6,887,384 B1 | 5/2005 | Frechet et al. |
| 6,960,449 B2 | 11/2005 | Wang et al. |
| 7,033,747 B2 | 4/2006 | Gordon et al. |
| 7,157,049 B2 | 1/2007 | Valencia et al. |
| 7,312,085 B2 | 12/2007 | Chou et al. |
| 7,332,326 B1 | 2/2008 | Kellogg et al. |
| 7,758,810 B2 | 7/2010 | Lee et al. |
| 8,337,775 B2 | 12/2012 | Pugia et al. |
| 8,945,914 B1 | 2/2015 | Schaff et al. |
| 8,962,346 B2 | 2/2015 | Schaff et al. |
| 9,186,668 B1 | 11/2015 | Schaff et al. |
| 9,244,065 B1 | 1/2016 | Schaff et al. |
| 9,304,128 B1 | 4/2016 | Koh et al. |
| 9,304,129 B2 | 4/2016 | Schaff et al. |
| 9,500,579 B1 | 11/2016 | Sommer et al. |
| 9,702,871 B1 | 7/2017 | Koh et al. |
| 2001/0055812 A1 | 12/2001 | Mian et al. |
| 2002/0098535 A1 | 7/2002 | Wang et al. |
| 2002/0106786 A1 | 8/2002 | Carvalho et al. |
| 2002/0137068 A1 | 9/2002 | Haugland et al. |
| 2002/0151043 A1 | 10/2002 | Gordon |
| 2002/0153251 A1 | 10/2002 | Sassi et al. |
| 2002/0164659 A1 | 11/2002 | Rao et al. |
| 2002/0170825 A1 | 11/2002 | Lee et al. |
| 2003/0013203 A1 | 1/2003 | Jedrzejewski et al. |
| 2003/0124719 A1 | 7/2003 | Woodside |
| 2003/0203504 A1 | 10/2003 | Hefti |
| 2004/0072278 A1 | 4/2004 | Chou et al. |
| 2005/0186685 A1 | 8/2005 | Kange et al. |
| 2005/0215410 A1 | 9/2005 | Merino et al. |
| 2005/0282220 A1 | 12/2005 | Prober et al. |
| 2006/0171654 A1 | 8/2006 | Hawkins et al. |
| 2008/0108047 A1 | 5/2008 | Woodside |
| 2008/0149484 A1 | 6/2008 | Tolley et al. |
| 2009/0004059 A1 | 1/2009 | Pugia et al. |
| 2009/0069554 A1 | 3/2009 | Finne |
| 2009/0209402 A1 | 8/2009 | Andersson |
| 2009/0325186 A1 | 12/2009 | Hinnah et al. |
| 2010/0068754 A1 | 3/2010 | Kirakossian |
| 2010/0120596 A1 | 5/2010 | Froman et al. |
| 2010/0151560 A1 | 6/2010 | Wo et al. |
| 2011/0045958 A1 | 2/2011 | Pedrazzini |
| 2013/0260447 A1 * | 10/2013 | Link .......... G01N 1/38 435/287.2 |
| 2014/0273241 A1 | 9/2014 | Ochranek et al. |
| 2015/0360225 A1 | 12/2015 | Schaff et al. |
| 2016/0061829 A1 | 3/2016 | Schaff et al. |
| 2016/0178619 A1 | 6/2016 | Koh et al. |

OTHER PUBLICATIONS

U.S. Appl. No. 13/423,008, filed Mar. 16, 2012, Koh et al.
U.S. Appl. No. 13/941,186, filed Jul. 12, 2013, Koh et al.
U.S. Appl. No. 14/090,040, filed Nov. 26, 2013, Koh et al.
U.S. Appl. No. 14/957,405, filed Dec. 2, 2015, Koh.
U.S. Appl. No. 15/616,740, filed Jun. 7, 2017, Koh et al.
U.S. Appl. No. 15/669,426, filed Aug. 4, 2017, Phaneuf et al.
U.S. Appl. No. 15/704,860, filed Sep. 14, 2017, Koh et al.
Abi-Samra et al., "Infrared controlled waxes for liquid handling and storage on a CD-microfluidic platform", Lab on a Chip, 2011, vol. 11, pp. 723-726.
Ahanotu et al., "*Staphylococcal enterotoxin* B as a biological weapon: recognition, management, and surveillance of *Staphylococcal enterotoxin*", Applied Biosafety, 2006, vol. 11 (3), pp. 120-126.
Albrecht et al., "Micro free-flow IEF enhanced active cooling and functionalized gels", Electrophoresis, 2006, vol. 27, pp. 4960-4969.
Amersham Biosciences AB, "Percoll: Methodology and Applications", Handbook No. 18-1115-69 (Ed. AC), 2001, Uppsala, Sweden, pp. 1-84.
Amukele et al., "Ricin A-chain activity on stem-loop and unstructured DNA substrates", Biochemistry, 2005, vol. 44(11), pp. 4416-4425.
Andersson et al., "Parallel nanoliter microfluidic analysis system", Analytical Chemistry, 2007, vol. 79(11), pp. 4022-4030.
Baldwin, "How Hofmeister ion interactions affect protein stability", Biophysical Journal, 1996, vol. 71, pp. 2056-2063.
Berlier et al., "Quantitative comparison of long-wavelength Alexa Fluor dyes to Cy dyes: fluorescence of the dyes and their bioconjugates", Journal of Histochemistry and Cytochemistry, 2003, vol. 51(12), pp. 1699-1712.
Berry et al., "One-step purification of nucleic acid for gene expression analysis via immiscible filtration assisted by surface tension", Lab on a Chip, 2011, vol. 11(10), pp. 1747-1753.
Boyko et al., "Cell-free DNA—a marker to predict ischemic brain damage in a rat stroke experimental model", Journal of Neurosurgery and Anesthesiology, 2011, vol. 23(3), pp. 222-228.
Brigotti et al., "Shiga toxin 1 acting on DNA in vitro is a heat-stable enzyme not requiring proteolytic activation", Biochimie Journal, 2004, vol. 86(45), pp. 305-309.
Buck et al., "Design strategies and performance of custom DNA sequencing primers", Biotechniques, 1999, vol. 27(3), pp. 528-536.
Carbera et al., "Formation of natural pH gradients in a microfluidic device under flow conditions: model and experimental validation", Analytical Chemistry, 2001, vol. 73(3), pp. 658-666.
Carney, "Rapid diagnostic tests employing latex particles", Analytical Proceedings,1990, vol. 27, pp. 99-100.
Churchill et al., "Detection of Listeria monocytogenes and the toxin listeriolysin O in food", Journal of Microbiological Methods, 2006, vol. 64(2), pp. 141-170.
Cui et al., "Multistage isoelectric focusing in a polymeric microfluidic chip", Analytical Chemistry, 2005, vol. 77(24), pp. 7878-7886.
Curtis et al., "A molecular approach to bioseparations: protein-protein and protein-salt interactions", Chemical Engineering Science, 2006, vol. 61, pp. 907-923.
Czeiger et al., "Measurement of circulating cell-free DNA levels by a new simple fluorescent test in patients with primary colorectal cancer", American Journal of Clinical Pathology, 2011, vol. 135(2), pp. 264-270.
Das et al., "Effects of separation length and voltage on isoelectric focusing in a plastic microfluidic device", Electrophoresis, 2006, vol. 27(18), pp. 3619-3626.
Endo et al., "RNA N-glycosidase activity of ricin A-chain. Mechanism of action of the toxic lectin ricin on eukaryotic ribosomes", The Journal of Biological Chemistry, 1987, vol. 262(17), pp. 8128-8130.
Fologea et al, "Detecting single stranded DNA with a solid state nanopore", Nano Letters, 2005, vol. 5(10), pp. 1905-1909.
Glorikian et al., "Microfluidics for IVDS—Smart consumable product development: implications for molecular diagnostics", DX Directions 2010, Spring, pp. 12-16.

(56) References Cited

OTHER PUBLICATIONS

Goldshtein et al., "A rapid direct fluorescent assay for cell-free DNA quantification in biological fluids", Annals of Clinical Biochemistry, 2009, vol. 46(Pt 6), pp. 488-494.

Görg et al., "Recent developments in two-dimensional gel electrophoresis with immobilized pH gradients: wide pH gradients up to pH 12, longer separation distances and simplified procedures", Electrophoresis, 1999, vol. 20(4-5), pp. 712-717.

Görg et al., "The current state of two-dimensional electrophoresis with immobilized pH gradients", Electrophoresis, 2000, vol. 21(6), pp. 1037-1053.

Gorkin et al., "Centrifugal microfluidics for biomedical applications", Lab on a Chip; 2010, vol. 10, pp. 1758-1773.

Gusev et al., "Capillary columns with in situ formed porous monolithic packing or micro high-performance liquid chromatography and capillary electrochromatography", Journal of Chromatography A, 1999, vol. 855(1), pp. 273-290.

Hatch et al., "Integrated preconcentration SDS-PAGE of proteins in microchips using photopatterned cross-linked polyacrylamide gels", Analytical Chemistry, 2006, vol. 78(14), pp. 4976-4984.

Herr et al., "Microfluidic immunoassays as rapid saliva-based clinical diagnostics", Proceedings of the National Academy of Science USA, 2007, vol. 104(13), pp. 5268-5273.

Herr et al., "On-chip coupling of isoelectric focusing and free solution electrophoresis for multidimensional separations", Analytical Chemistry, 2003, vol. 75(5), pp. 1180-1187.

Holmberg et al., "Depurination of A4256 in 28 S rRNA by the ribosome-inactivating proteins from barley and ricin results in different ribosome conformations", Journal of Molecular Biology, 1996, vol. 259(1), pp. 81-94.

Holmes et al., "Leukocyte analysis and differentiation using high speed microfluidic single cell impedance cytometry", Lab on a Chip, 2009, vol. 9, pp. 2881-2889.

Huang et al., "The primary structure of Staphylococcal enterotoxin B: III. The cyanogen bromide peptides of reduced and aminoethylated enterotoxin B, and the complete amino acid sequence", Journal of Biological Chemistry, 1970, vol. 245(14), pp. 3518-3525.

Huang et al., "Microfabrication of a tapered channel for isoelectric focusing with thermally generated pH gradient," Electrophoresis, 2002, vol. 23(20), pp. 3504-3510.

IVD Technology, "Microfludic applications for IVDs", DX Directions, 2010, Spring, pp. 1-26.

Invitrogen Life Technologies, "ZOOM IEF Fractionator, Instructional Manual", Catalog Nos. ZF10001 & ZF10002, Version C, Jul. 2004 (64 pp.).

Kim et al., "Fully integrated lab-on-a-disc for nucleic acid analyisis of food-borne pathogens", Analytical Chemistry, 2014, vol. 86, pp. 3841-3848.

Koh et al., "Centrifugal microfluidic platform for ultrasensitive detection of botulinum toxin", Analytical Chemistry, 2015, vol. 81, pp. 922-928.

Lee et al., "Fully integrated lab-on-a-disc for simultaneous analysis of biochemistry and immunoassay from whole blood", Lab on a Chip, 2011, vol. 11(1), pp. 70-78.

Lee et al., "A fully automated immunoassay from whole blood on a disc", Lab on a Chip, 2009, vol. 9(11), pp. 1548-1555.

Lim et al., "Bead-based microfluidic immunoassays: The next generation", Biosensors and Bioelectronics, 2007, vol. 22(7), pp. 1197-1204.

Lim et al., "Rapid isoelectric trapping in a micropreparative-scale multicompartment electrolyzer", Electrophoresis, 2007, vol. 28(12), pp. 1851-1859.

Lo et al., "Photopolymerized diffusion-defined polyacrylamide gradient gels for on-chip protein sizing", Lab on a Chip, 2008, vol. 8(8), pp. 1273-1279.

Lo et al., "Plasma DNA as a prognostic marker in trauma patients", Clinical Chemistry, 2000, vol. 46(3), pp. 319-323.

Long et al., "Integrated of nanoporous membranes for sample filtration/preconcentration in microchip electrophoresis", Electrophoresis, 2006, vol. 27(24), pp. 4927-4934.

Madou et al., "Lab on a CD", Annual Review of Biomedical Engineering, 2006, vol. 8, pp. 601-628.

Maes et al., "Comparison of sample fixation and the use of LDS-751 or anti-CD45 or leukocyte identification in mouse whole blood for flow cytometry", Journal of Immunological Methods, 2007, vol. 319(1-2), pp. 79-86.

Mcbain et al., "Polyethyleneimine functionalized iron oxide nanoparticles as agents for DNA delivery and transfection", Journal of Material Chemistry, 2007, vol. 17(24), pp. 2561-2565.

Melting Temperature Calculation. Retrieved on asf from the internet: http://www.biophp.org/minitools/melting_temperature/demo.php?primer-CGT+TAC+CCG+CAG&basic-1&NearestNeighbor=1&cp=200&cs=50&cmg=0.

Min et al., "Functional integration of DNA purification and concentration into a real time micro-PCR chip", Lab on a Chip, 2011, vol. 11(2), pp. 259-265.

O'Farrell, "High resolution two-dimensional electrophoresis of proteins", Journal of Biological Chemistry, 1975, vol. 250(10), pp. 4007-4021.

Ogle et al., "Preparative-scale isoelectric trapping separations using a modified Gradiflow unit", Journal of Chromatography A, 2002, vol. 979(1-2), pp. 155-161.

Price et al., "Light-scattering immunoassay", in Principles and Practice Immunoassay (Second Ed., C.P. Price & D.J. Newman, eds.), 1997, Stockton Press (New York, NY), Chap. 18, pp. 445-480.

PubChem Search results for "2,3-dihydroxypropyl octanoate," retrieved on Oct. 5, 2016 from https://www.ncbi.nlm.nih.gov/pcompound/?term=2%2C3-dihydroxypropyl+octanoate (4 pp.).

PubChem Entry for "TWEEN 20," retrieved on Oct. 4, 2016 from https://pubchem.ncbi.nlm.nih.gov/compound/Tween_20#section-Names-and-identifiers (2 pp.).

Rhodes et al., "Plasma DNA concentration as a predictor of mortality and sepsis in critically ill patients", Critical Care, 2006, vol. 10(2), Article R60 (pp. 1-7).

Riahi et al., "Molecular detection of bacterial pathogens using microparticle enhanced double-stranded DNA probes", Analytical Chemisty, 2011, vol. 83(16), pp. 6349-6354 and Supporting Information (8 pp.).

Rider et al., "A B cell-based sensor for rapid identification of pathogens", Science, 2003, vol. 301, pp. 213-215.

Riegger et al., "Read-out concepts for multiplexed bead-based fluorescence immunoassays on centrifugal microfluidic platforms", Sensors and Actuators A—Physical, 2006, vol. 126, pp. 455-462.

Righetti, "The Alpher, Bethe, Gamow of isoelectric focusing, the alpha—Centaury of electrokinetic methodologies—part I", Electrophoresis, 2006, vol. 27(5-6), pp. 923-938.

Righetti, "The Alpher, Bethe and Gamow of IEF, the alpha—Centaury of electrokinetic methodologies—part II: immobilized pH gradients", Electrophoresis, 2007, vol. 28(4), pp. 545-555.

Saukkonen et al., "Cell-free plasma DNA as a predictor of outcome in severe sepsis and septic shock", Clinical Chemistry, 2008, vol. 54(6), pp. 1000-1007.

Schaff et al., "Whole blood immunoassay based on centrifugal bead sedimentation", Clinical Chemistry, 2011, vol. 57(5), pp. 753-761.

Schembri et al., "Portable simultaneous multiple analyte whole-blood analyzer for point-of-care testing", Clinical Chemistry, 1992, vol. 38(9), pp. 1665-1670.

Schneider et al., "Characterization of EBV-genome negative "null" and "t" cell lines derived from children with acute lymphoblastic leukemia and leukemic transformed non-Hodgkin lymphoma", International Journal of Cancer, 1977, vol. 19(5), pp. 621-626.

Sigma-Aldrich product page for TWEEN 20, archived from Jun. 28, 2012, retrieved on Oct. 5, 2016 from https://web.archive.org/web/20120628080753/http://www.sigmaaldrich.com/catalog.product/sial/p1379?ang-en®ion= (43 pp.).

Sommer et al., "On-chip isoelectric focusing using photopolymerized immobilized pH gradients", Analytical Chemistry, 2008, vol. 80(9), pp. 3327-3333.

Suzuki et al., "Experimental optimization of probe length to increase the sequence specificity of high-density oligonucleotide microarrays", BMC Genomics, 2007, vol. 8, Art. 373 (13 pages).

(56) References Cited

OTHER PUBLICATIONS

Tan et al., "Miniaturized capillary isoelectric focusing in plastic microfluidic devices", Electrophoresis, 2002, vol. 23(20), pp. 3638-3645.

Yu et al., "Bioinformatic processing to identify single nucleotide polymorphism that potentially affect Ape1 function", Mutation Research/Genetic Toxicology and Environmental Mutagenesis, 2011, vol. 722(2), pp. 140-146.

Zhang et al., "A new biodosimetric method: branched DNA-based quantitative detection of B1 DNA in mouse plasma", British Journal of Radiology, 2010, vol. 83, pp. 694-701.

Ziegler et al., "Circulating DNA: a new diagnostic gold mine?", Cancer Treatment Reviews, 2002, vol. 28, pp. 255-271.

Zilberstein et al., "Parallel isoelectric focusing chip", Proteomics, 2004, vol. 4(9), pp. 2533-2540.

Zilberstein et al., "Parallel isoelectric focusing II", Electrophoresis, 2004, vol. 25(21-22), pp. 3643-3651.

Zilberstein et al., "Parallel processing in the isoelectric focusing chip", Electrophoresis, 2003, vol. 24(21), pp. 3735-3744.

Zuo et al., "A method for global analysis of complex proteomes using sample prefractionation by solution isoelectrofocusing prior to two-dimensional electrophoresis", Analytical Biochemistry, 2000, vol. 284(2), pp. 266-278.

\* cited by examiner

METHOD AND APPARATUS FOR PURIFYING NUCLEIC ACIDS AND PERFORMING POLYMERASE CHAIN REACTION ASSAYS USING AN IMMISCIBLE FLUID

CROSS-REFERENCE TO RELATED APPLICATION

This application is a divisional of prior application Ser. No. 14/090,040, filed Nov. 26, 2013, which is incorporated herein by reference in its entirety.

STATEMENT REGARDING RESEARCH & DEVELOPMENT

This invention was made with Government support under Contract No. DE-NA0003525 awarded by the United States Department of Energy/National Nuclear Security Administration. The Government has certain rights in the invention.

TECHNICAL FIELD

Embodiments of the invention relate generally to purifying nucleic acids with immiscible fluids and conducting polymerase chain reaction assays.

BACKGROUND

Polymerase chain reaction (PCR) assays are generally used for molecular diagnostics due to the sensitivity and specificity of the assay. PCR is a technique which allows a single copy or piece of DNA to be replicated, amplifying the amount of DNA in a sample to be analyzed. In this manner, even single nucleotide changes can be detected through well-constructed PCR assays. PCR generally involves thermal cycling of a sample, e.g. repeated heating and cooling of the sample, to allow for DNA melting and enzymatic replication. The thermal cycling generally takes place in the presence of PCR reagents. PCR reagents generally include primers (e.g. DNA fragments complementary to a target region of interest) and DNA polymerase.

Systems are available for performing PCR with purified nucleic acid inputs. Non-disk-based microfluidic devices integrating sample preparation with amplification and detection exist. The sample input generally requires purified cell populations from culture, suspended in buffers such as PBS; environmental samples often important for biodefense are unable to be analyzed on the platform. Commercial systems for analysis of clinical samples by PCR on microfluidic systems are available. These systems typically require extensive sample preparation before introduction into the system.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, electronic components, circuits, control signals, timing protocols, and software operations have not been shown in detail in order to avoid unnecessarily obscuring the described embodiments of the invention.

Figure 1:
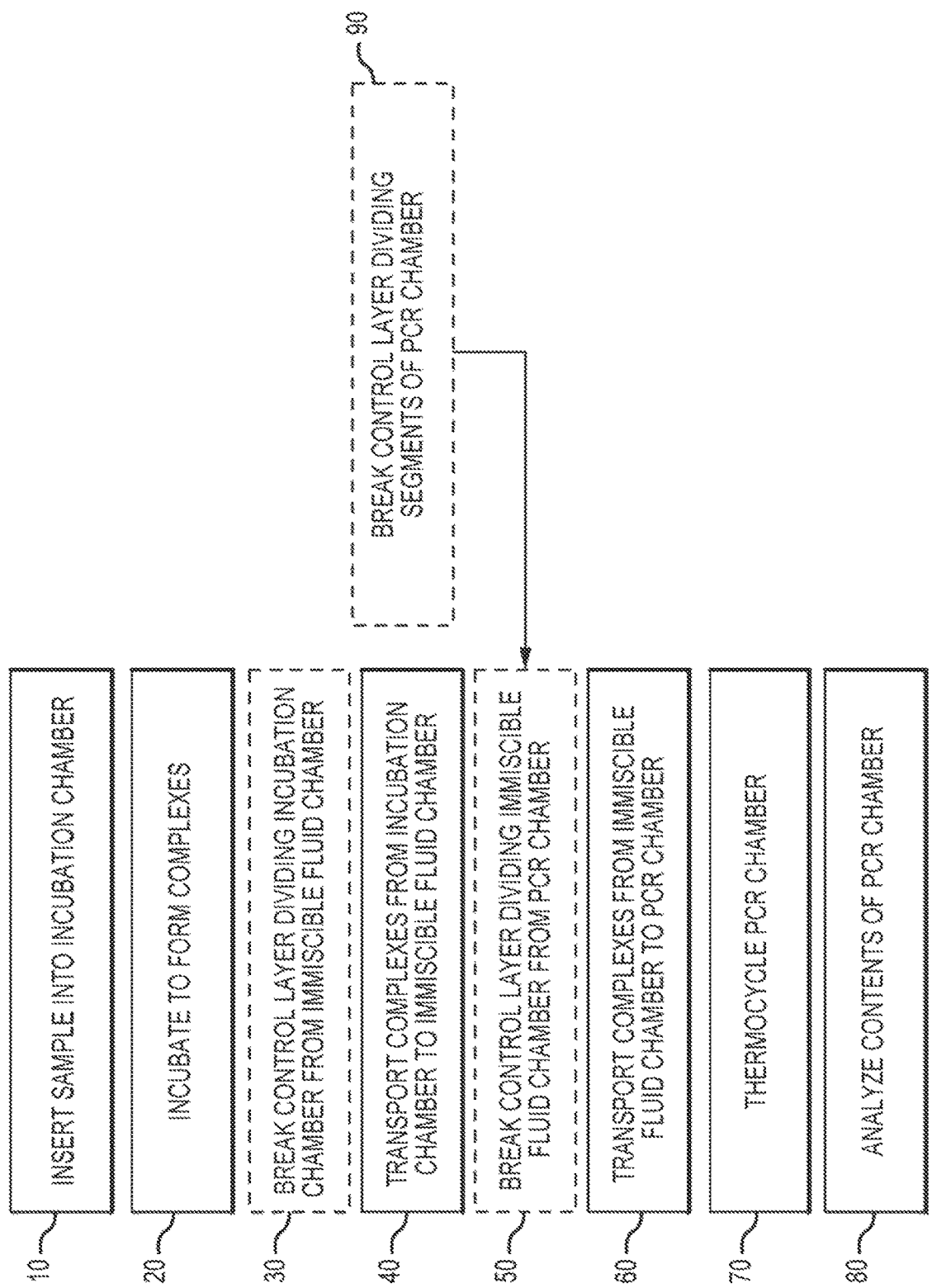
FIG. 1 is a flowchart illustrating a method in accordance with embodiments of the present invention.

FIG. 1 is a flowchart illustrating a method in accordance with embodiments of the present invention. At operation 10, a sample is provided to an incubation chamber with beads and a lysis buffer. The sample may be provided to the incubation chamber in generally any manner used to provide sample to a device. Examples include, but are not limited to, pipetting, injection, or fluid transport including, but not limited to, pressure-driven flow. The incubation chamber may contain beads and a lysis buffer. In some embodiments, the beads and lysis buffer may be provided to the incubation chamber, e.g. using pipetting, injection, or pressure-driven flow, prior to or at the same time as the sample. In other embodiments, the lysis buffer and beads may be pre-loaded in the incubation chamber. A variety of samples may be utilized in accordance with embodiments of the present invention. Generally the sample is a fluid (e.g. a liquid) containing, or which may contain, DNA or DNA fragments which may be amplified using PCR. Samples of interest include, but are not limited to, blood, serum, saliva, and combinations thereof. The sample may be of clinical, environmental, animal, food, water, or other origin. The lysis buffer may be any lysis buffer that is appropriate, or expected to be appropriate, for the sample.

The beads may be macroporous silica microparticles in some examples. These microparticles, through the use of large volumes of porogens during manufacture, may have very large surface area-to-volume ratios. One gram of particles typically has several hundred square meters of surface area. In other embodiments, the beads may have a silica surface which binds to nucleic acids in the presence of high salt. The beads may be polystyrene or have a polystyrene surface that is modified with a surface chemistry which binds nucleic acids in high salt conditions in some examples. A variety of particle sizes may be utilized in accordance with embodiments of the present invention including diameters from 0.5 μm-10 μm, with 5 μm being preferred in some embodiments. Other diameter particles may be used.

Figure 7:
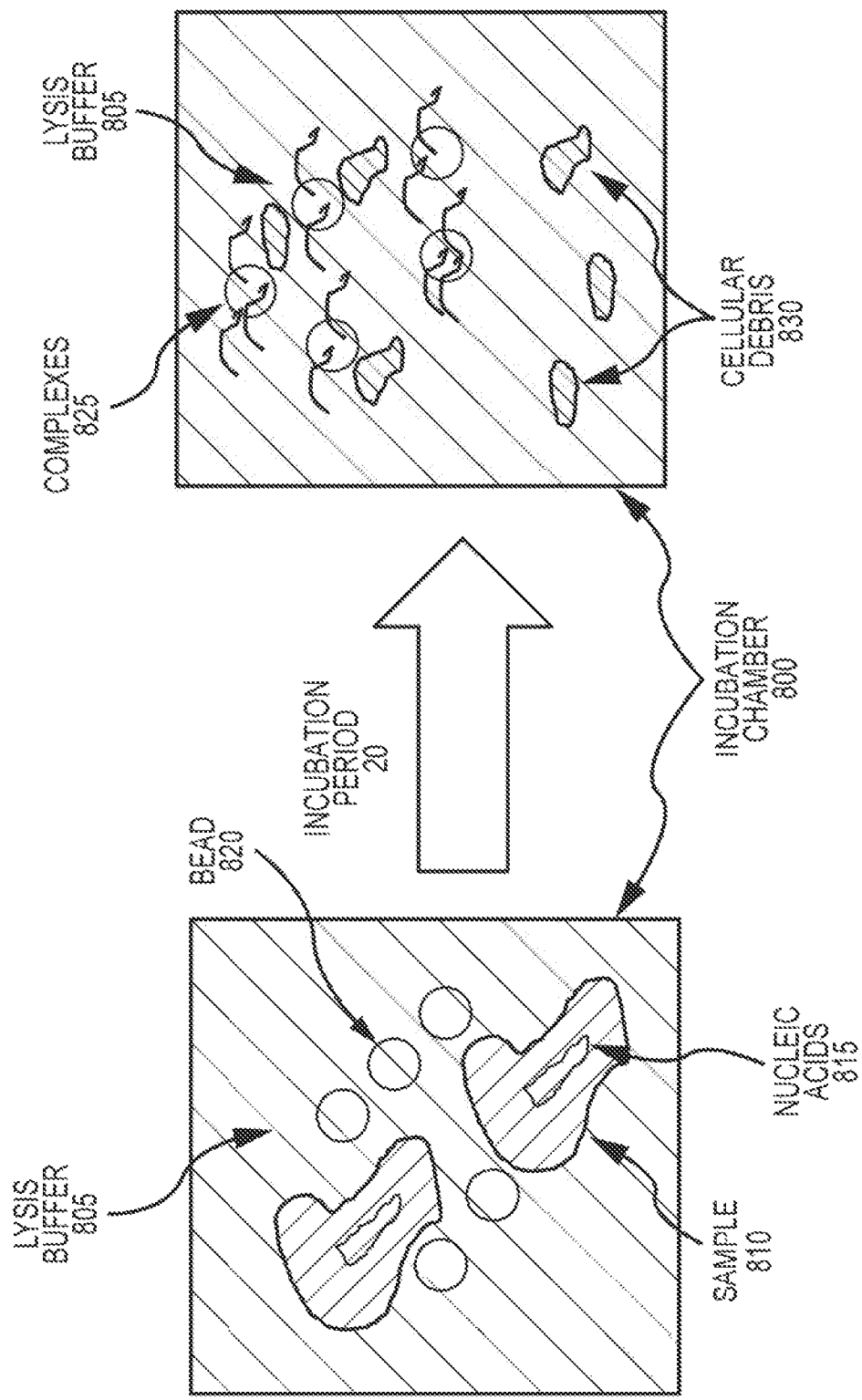
FIG. 7 is a schematic illustration of complex formation in accordance with embodiments of the present invention.

In operation 20, the contents of the incubation chamber are allowed to incubate for a period of time. The period of time is selected to allow for sufficient sample lysis to occur. In some example, the period of time is between 10 and 15 minutes at room temperature. The period of time may vary in accordance with sample type, temperature, quantity, and design of the incubation chamber geometry, for example. FIG. 7 is a schematic illustration of complex formation in accordance with embodiments of the present invention. A sample 810 contains nucleic acids 815 in a lysis buffer 805 with the silica beads 820 in the incubation chamber 800.

Under lysis buffer conditions (e.g. high salt) in the incubation chamber, the nucleic acids in the sample may be bound to the silica beads, forming complexes. Accordingly, following incubation 20, cells may be lysed and nucleic acids 815 bound to beads 820, forming complexes 825. In some embodiments, cellular debris 830 may be formed during lysis. In some embodiments, cell lysis may not be required, a lysate buffer may not be used. In some embodiments, nucleic acids may be bound to beads in a sample preparation step not associated with the device in use, and provided directly to a chamber of a device.

In operation 40, complexes are transported from the incubation chamber to a chamber containing an immiscible fluid. A variety of fluid transport mechanisms may be used to effect transport of the complexes including, but not limited to, centrifugal force, gravitational force, electrophoretic transport, or combinations thereof. Optionally, the incubation chamber and immiscible fluid chamber may be separated by a control layer. The control layer may fluidically isolate the incubation chamber from the immiscible fluid chamber (e.g. by forming a barrier between the chambers), and the control layer may be broken during operation 30 when or prior to when transport of the complexes between the chambers is desired. Examples of control layers include, but are not limited to, valves, sacrificial layers, breakable layers (e.g. membranes), or combinations thereof.

Figure 8:
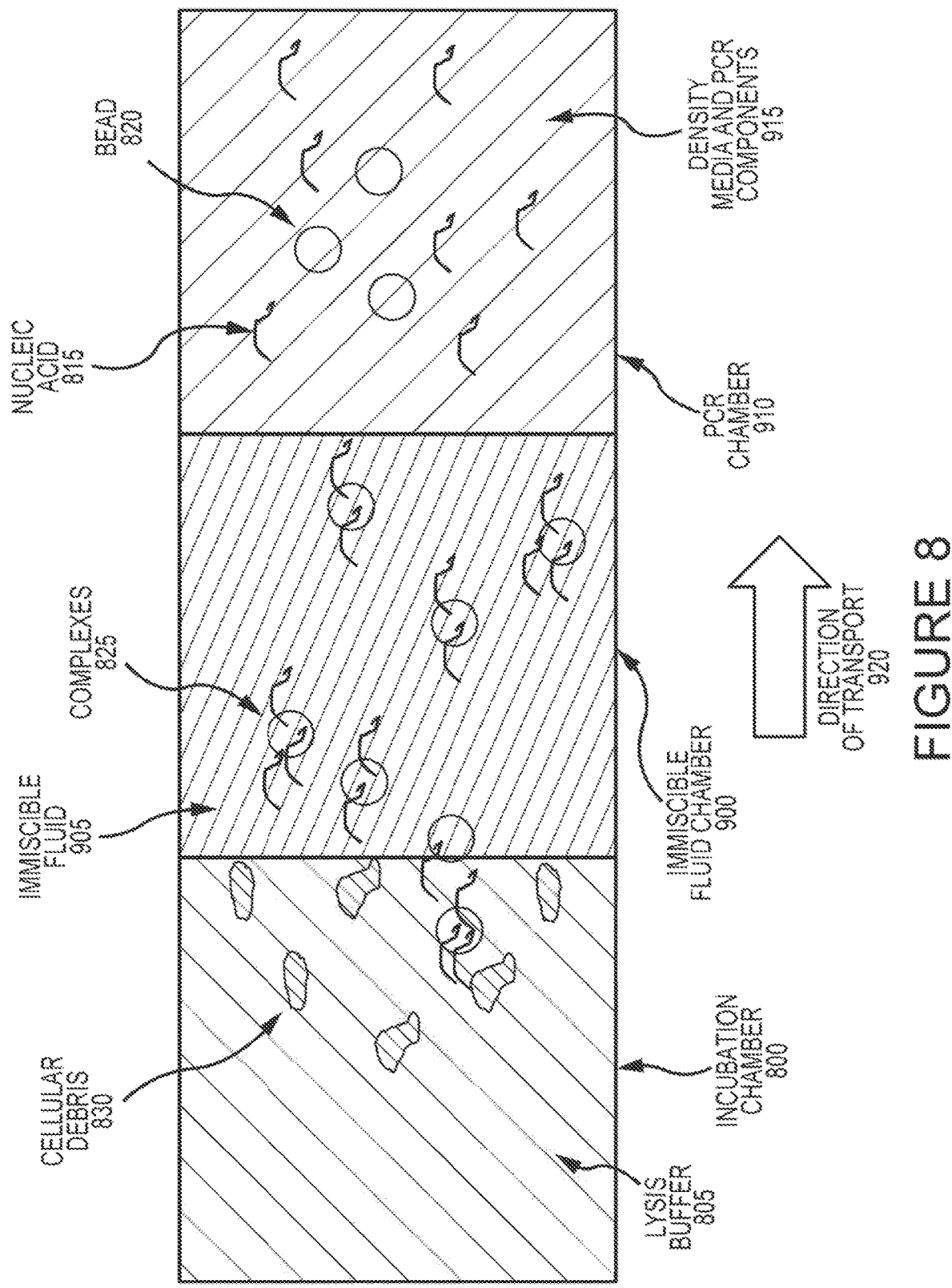
FIG. 8 is a schematic illustration of complex transport in accordance with embodiments of the present invention.

FIG. 8 is a schematic illustration of complex transport in accordance with embodiments of the present invention. The immiscible fluid 905 generally excludes the lysis buffer 805, and/or interfering compounds of the lysis buffer, for example, cellular debris 830, from transport into the immiscible fluid chamber 900 through hydrophobic interactions, and/or a combination of density and hydrophobic interactions. The immiscible fluid chosen may be denser than the cellular debris, the lysis buffer, or combinations thereof. Accordingly, as a centrifugal or gravitational force is applied to a device containing the incubation and immiscible fluid chambers, the cellular debris, lysis buffer, and/or combinations thereof, may be physically excluded from transport into the immiscible fluid chamber due to their density. The beads used to form the complexes 825 may be denser than the immiscible fluid. Accordingly, the beads may be transported through the immiscible fluid responsive to a centrifugal or gravitational force, or combinations thereof. Additionally or instead, the immiscible fluid may contain perfluorcompounds, which may exclude water and/or water-based compounds from the lysis buffer from transport into the immiscible fluid. In this manner, the beads may be washed of interfering compounds and the nucleic acids bound to the beads may be chemically isolated from the lysate and other matrix components, thus providing purified complexes including nucleic acids in the immiscible fluid. Suitable immiscible fluids include, but are not limited to: oil, perfluorohydrocarbons, partially fluorinated hydrocarbons, silicone-based liquids, and immiscible aqueous mixtures, such as a combination of poly(ethylene glycol) and dextran.

The complexes 825 may be transported through the immiscible fluid 905, which may advantageously provide washing and isolation benefits in some examples. The complexes 825 may be transported to a PCR chamber 910 in operation 60, as shown schematically in FIG. 8. Optionally, the immiscible fluid chamber 900 and the PCR chamber 910 can be separated by a control layer (Not shown in FIG. 8). Examples of control layers include, but are not limited to, valves, sacrificial layers, breakable layers (e.g. membranes), or combinations thereof. The control layer generally may provide a fluidic barrier between the immiscible fluid chamber 900 and the PCR chamber 910 but may be broken, opened, or combinations thereof to place the chambers in fluidic communication. The control layer, may be broken or otherwise opened when or prior to when transport of the complexes between the chambers is desired at operation 50.

The PCR chamber generally contains a density medium and PCR reagents (e.g. components necessary for PCR amplification). PCR reagents contained in the density medium may include, but are not limited to, DNA polymerase (such as Taq polymerase), deoxynucleoside triphosphates, magnesium, potassium, DNA template of the product to be amplified, DNA primers, and combinations thereof. In some example methods, the PCR reagents may be provided to the PCR chamber (e.g. by pipetting, injection, or other fluid transport technique). In other examples, the PCR reagents may already be provided in the PCR chamber. The PCR chamber may include a density medium 915, as shown in FIG. 8. The density medium any be an aqueous solution that may be low-salt, allowing nucleic acids 815 to desorb from the surface of the beads 820 for enhanced PCR efficiency in some examples. The density medium may contain Percoll™ or iodixanol in some examples. The PCR chamber may be thermocycled as appropriate for the chosen PCR assay in operation 70. Thermocycling may be achieved through the use of generally any heating and/or cooling elements, including but not limited to Peltier thermoelectric elements. After cycles of amplification, labeling agents, which may be provided in the PCR chamber, bind to the amplified product, if present, and the contents of the PCR chamber may be analyzed at operation 80. A variety of labeling agents may be used including those that facilitate optical, electrical, electrophoretic detection, or combinations thereof. Optical methods may include fluorescence, total internal reflection fluorescence (TIRF), turbidimetric, chemiluminescent, or bioluminescence. In one embodiment, an electrical detection method may be through reduction potential measurements. In some examples, the labeling agents may be dyes that may be detected via laser-induced fluorescence. Labeling agents may include SYBR® green, Syto™ 9, SYBR® Gold, or other appropriate molecular beacons or probes. In some examples, the labeling agents may intercalate with the amplified product, if present.

In some examples, the PCR chamber may be divided into two segments by a control layer (e.g. a valve, sacrificial, or other breakable layer). The first segment may contain freeze dried or otherwise shelf-stable PCR reagents (e.g. DNA polymerase) and the second segment may contain the density medium. Before the complexes are transported from the immiscible fluid chamber to the PCR chamber, the control layer between the two segments may be broken in operation 90, causing the PCR reagents and the density medium to be combined. In this manner, a shelf-stable device may be provided in some examples which includes the reagents for performing methods described herein, and an end user need only provide the sample into the device. In some examples, the end user need not provide the PCR reagents, lysis buffer, or beads, or combinations thereof. Instead, those components may be provided to the user with (e.g. contained in) the device in some examples.

Figure 2:
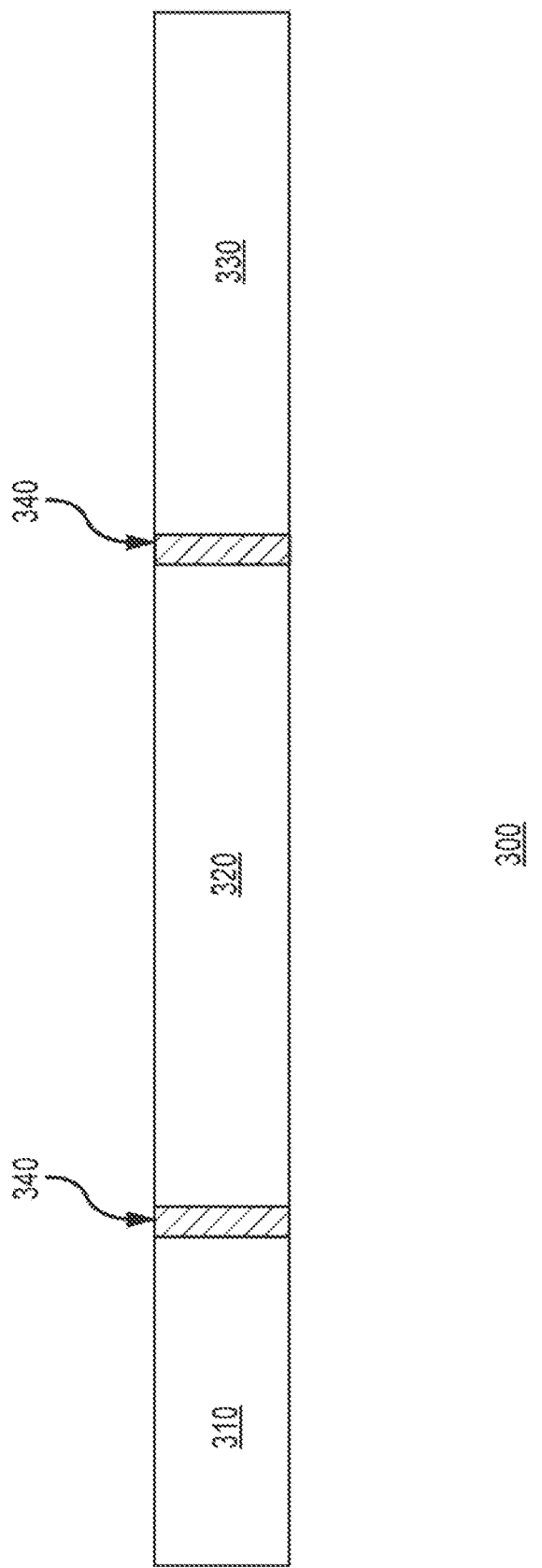
FIG. 2 is a schematic illustration of an apparatus arranged in accordance with embodiments of the present invention.

FIG. 2 is a schematic illustration of an apparatus arranged in accordance with embodiments of the present invention. The chambers 310, 320, and 330 are shown. The chambers may generally be implemented using any arrangement of fluidic features suitable for holding the described components. For example, the chambers may be separate features or may be different segments of a same fluid channel or other structure. The incubation chamber 310 may contain lysis buffer, beads, and sample. The immiscible fluid is contained in chamber 320, and the density medium and PCR components are in chamber 330. The optional control layers (e.g. membranes) are shown at 340 and 350. Chamber 330 may be further divided into two segments, as described above, although not shown in FIG. 2, by another control layer with the freeze dried PCR components in one segment and the density medium in the other segment. Examples of the devices described herein, such as the device 300 of FIG. 2 may be implemented in a microfluidic system. Although not shown in FIG. 2, any number of additional components may also be included in systems described herein including, but not limited to, valves, pumps, inputs, outputs, mixers, heaters, or combinations thereof. The example shown in FIG. 2 is intended to represent a top-down view of a microfluidic device, with the inputs and outputs of a channel containing the chambers 310, 320, and 330 not shown.

Figure 3:
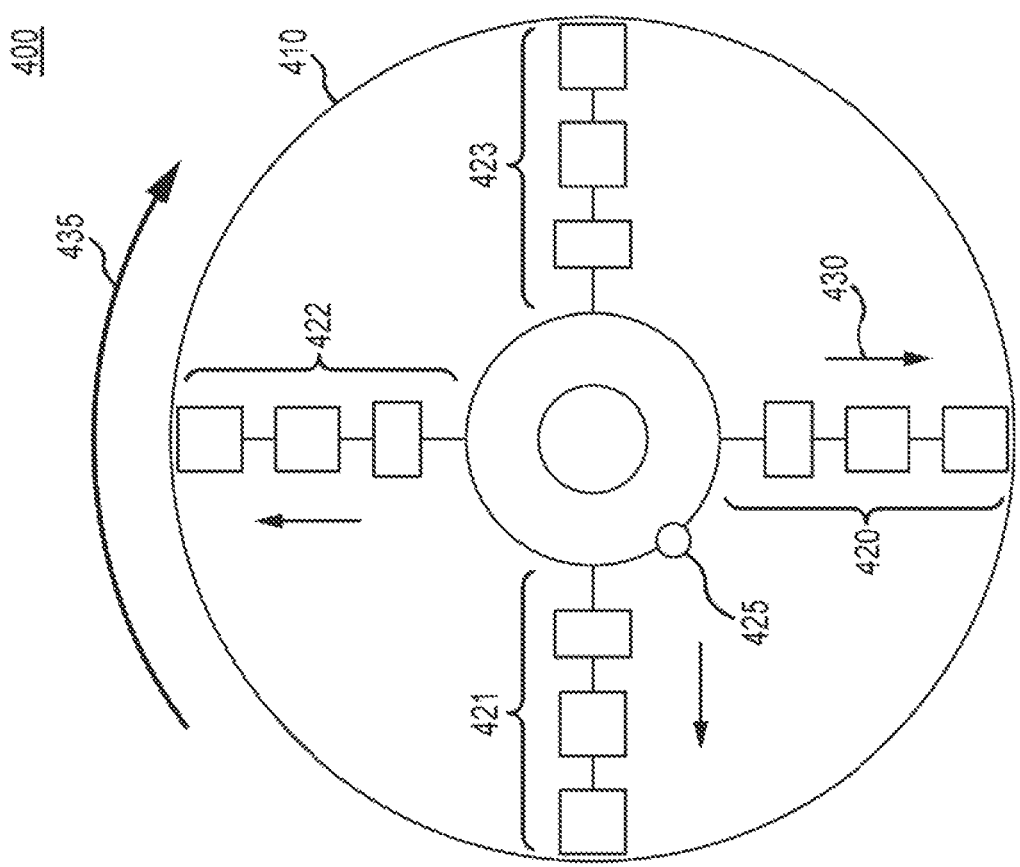
FIG. 3 is a schematic illustration of a microfluidic disk arranged in accordance with embodiments of the present invention.

FIG. 3 is a schematic illustration of a microfluidic disk 400 arranged in accordance with the embodiments of the present invention. The microfluidic disk 400 may include a substrate 410 which may at least partially define regions of assay areas 420-422. The microfluidic disk 400 may include a fluid inlet port 425 in fluid communication with the assay areas 420-422. Each assay area may include any variety of fluidic features and components, including but not limited to, channels, chambers, valves, pumps, etc. As shown in FIG. 3, each assay area includes an incubation chamber, an immiscible fluid chamber, and a PCR chamber. During operation, fluids including sample liquids, density media, and/or beads suspended in a fluid, may be transported using centrifugal force from an interior of the microfluidic disk 400 toward a periphery of the microfluidic disk 400 in a direction indicated by arrow 430. The centrifugal force may be generated by rotating the microfluidic disk 400 in the direction indicated by the arrow 435 or the opposite direction.

The substrate 410 may be implemented by using any of a variety of suitable substrate materials. In some embodiments, the substrate may be a solid transparent material. Transparent plastics, quartz, glass, fused-silica, PDMS, and other transparent substrates may be desired in some embodiments to allow optical observation of sample within the channels and chambers of the disk 400. In some embodiments, however, opaque plastic, metal, or semiconductor substrates may be used. In some embodiments, multiple materials may be used to implement the substrate 410. The substrate 410 may be made up of multiple layers. The substrate 410 may include surface treatments or other coatings, which may in some embodiments, enhance compatibility with fluids placed on the substrate 410. In some embodiments surface treatments or other coatings may be provided to control fluid interaction with the substrate 410. While shown as a round disk in FIG. 3, the substrate 410 may take substantially any shape, including square.

In some embodiments, the substrate 410 may itself be coupled to a motor for rotation. In some embodiments, the substrate may be mounted on another substrate or base for heating and/or rotation. For example, a microfluidic chip fabricated at least partially in a substrate may be mounted on another substrate for spinning. In some examples, the microfluidic chip may be disposable while the substrate or base it is mounted on may be reusable. In some examples, the entire disk may be disposable. In some examples, a disposable cartridge including one or more microfluidic channels may be inserted into the disk or other mechanical rotor that forms part of a detection system.

The substrate 410 may generally, at least partially, define a variety of fluidic features. The fluidic features may be microfluidic features. Generally, microfluidic, as used herein, refers to a system, device, or feature having a dimension of around 1 mm or less and suitable for at least partially containing a fluid. In some embodiments, 500 μm or less. In some embodiments, the microfluidic features may have dimensions of around 100 μm or less. Other dimensions may be used the substrate 410 may define one or more fluidic features, including any number of channels, chambers, inlet/outlet ports, or other features.

A fluid inlet port 425 may be provided to receive a fluid that may be analyzed using the microfluidic disk 400. The fluid inlet port 425 may have generally any configuration, and a fluid sample may enter the fluid inlet port 425 utilizing substantially any fluid transport mechanism, including pipetting, pumping, or capillary action. The fluid inlet port 425 may take substantially any shape. Generally, the fluid inlet port 425 is in fluid communication with at least one assay area 420, and may be in fluid communication with multiple assay areas 420-423 in FIG. 3. Generally, by fluid communication it is meant that a fluid may flow from one area to the other, either freely or using one or more transport forces and/or valves, and with or without flowing through intervening structures.

The assay area 420 generally may include one or more channels in fluid communication with the fluid inlet port 425. Although four assay areas 420-423 are shown in FIG. 4, generally any number may be present on the microfluidic disk 400.

As the microfluidic disk 400 is rotated in the direction indicated by the arrow 435 (or in the opposite direction), a centrifugal force may be generated. The centrifugal force may generally transport fluid from the inlet port 425 into one or more of the assay areas 420-423. Accordingly, the microfluidic disk 400 may be used to perform assays described herein.

Figure 4:
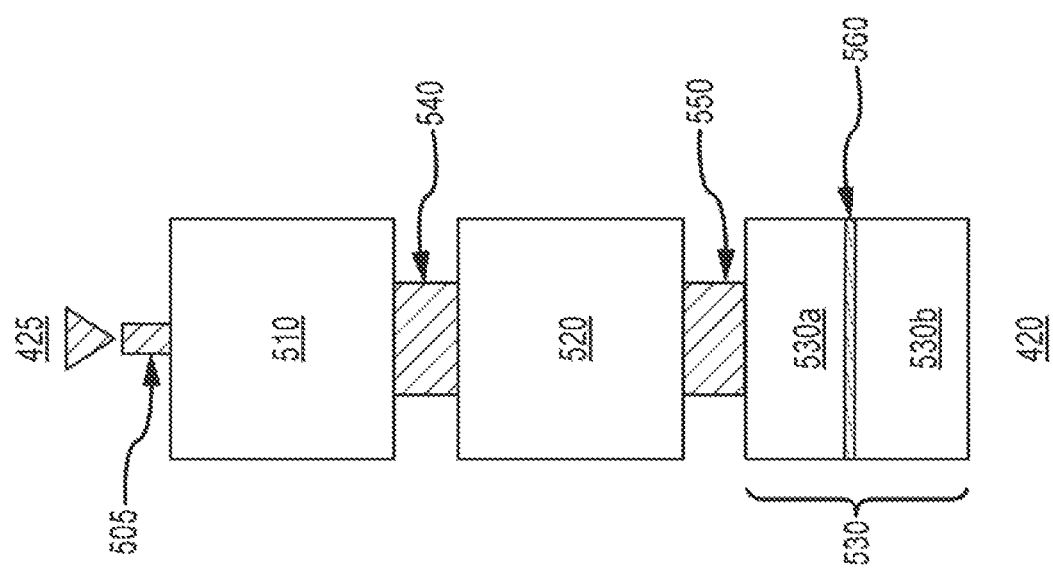
FIG. 4 is a schematic illustration of an apparatus arranged in accordance with embodiments of the present invention.

FIG. 4 is a schematic illustration of an assay area 420 of a microfluidic disk in accordance with an embodiment of the present invention. FIG. 4 provides a top-down view of an assay area. The assay area 420 includes a channel 505 in fluid communication with the fluid inlet port 425. The channel is in fluid communication with an incubation chamber 510. The incubation chamber 510 is in fluid communication to an immiscible fluid chamber 520. The fluid communication may be interrupted by a control layer 540 between the incubation chamber 510 and the immiscible fluid chamber 520. The immiscible fluid chamber 520 is in fluid communication to a PCR chamber 530. The fluid communication may be interrupted by a control layer 550 between the immiscible fluid chamber 520 and the PCR chamber 530. The PCR chamber may be further segmented into two section 530*a* and 530*b* in fluid communication with each other. The fluid communication may be interrupted by a control layer 560 between the segments. The control layers may be made of wax in some embodiments of the invention and may be broken by heating, for example. Other types of control layers may be used, including, for example, layers that may be punctured or otherwise broken. For example, plastic or other membranes may be used and a pin or other actuator may be deployed to break the membrane and create fluid communication in some examples. Transport of fluids between chambers 510, 520, and 530 may be achieved through centrifugal forces.

Figure 5:
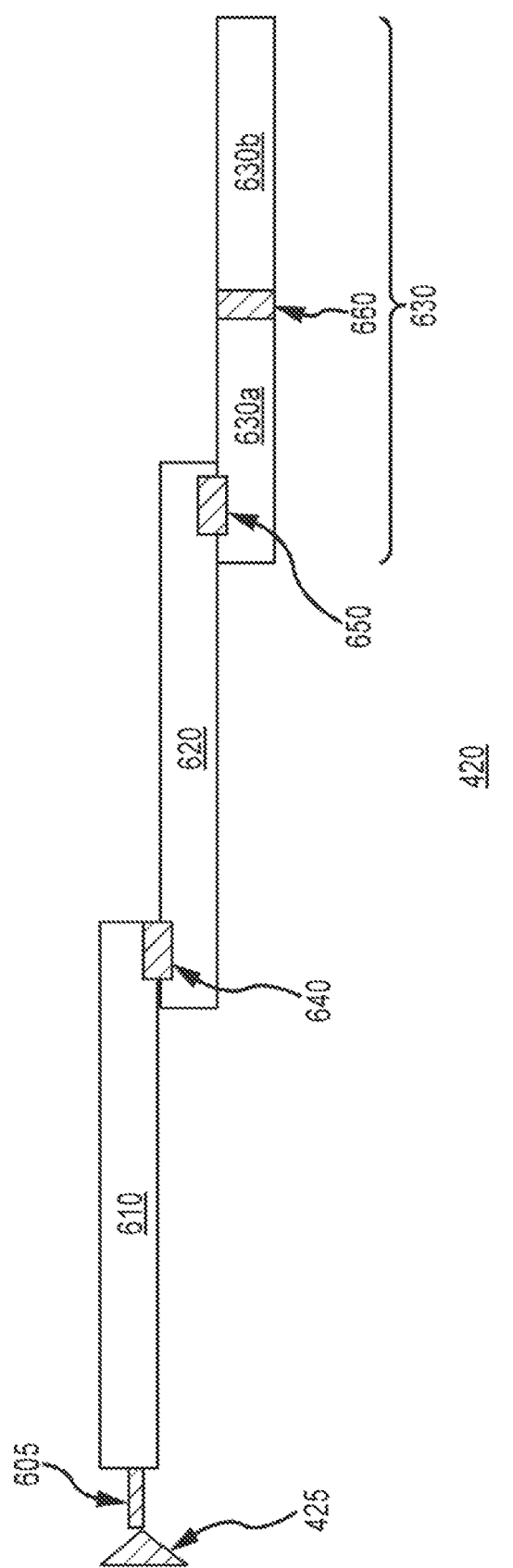
FIG. 5 is a schematic illustration of an apparatus arranged in accordance with embodiments of the present invention.

FIG. 5 is a schematic illustration of an assay area arranged in accordance with embodiments of the present invention. FIG. 5 is a cross-sectional view of an assay area, and may be used to implement the assay area 420 of FIG. 3. In FIG. 5, the bottom surface of the PCR chamber 630 may be near the same level as the bottom surface of the substrate 410. The bottom surface of the immiscible fluid chamber 620 may be within the substrate 410, but above the bottom surface of the PCR chamber 630. The incubation chamber 610 is at least partially defined by the substrate 410, and its bottom surface may be above the level of the immiscible fluid chamber 620. The chambers 610, 620, and 630 may be in fluid communication. Optionally, the fluid communication can be interrupted by control layers 640 and 650. Additionally, the PCR chamber 630 may be further segmented into two segments 630a and 630b in fluid communication with each other. The fluid communication between 630a and 630b may be interrupted by control layer 660.

FIG. 7 is a schematic illustration of a system according to an embodiment of the present invention. The system 700 may include the disk 400 of FIG. 4 with one or more assay areas 420. A motor 705 may be coupled to the disk 400 and configured to spin the disk 400, generating centrifugal forces. A detection module 710 may be positioned to detect signal from labeling agents in a detection region of the assay area 420. A heating element 715 may be positioned between the motor and the disk to heat the disk. A processing device 720 may be coupled to the motor 705, the detection module 710, and the heating element 715 and may provide control signals to those components. The processing device 720 may further receive electronic signals from the detection module 710 corresponding to the labeling agent signals received by the detection module 710. All or selected components shown in FIG. 7 may be housed in a common housing in some examples. Microfluidic disks, which may be disposable, may be placed on the motor of 705 and removed, such that multiple disks may be analyzed by the system 700.

The motor 705 may be implemented using a centrifugation and/or stepper motor. The motor 705 may be positioned relative to the detection module 710 such that, when the disk 400 is situated on the motor 705, the disk is positioned such that a detection region of the assay area 420 is exposed to the detection module 710.

The heating element of 715 may be implemented using a Peltier heating element. The heating element 715 may be positioned relative to the motor 705 such that it may heat the disk 400 both when the motor 705 is spinning the disk 400, and when it is not spinning the disk 400.

The detection module 710 may include a detector suitable for detecting signal from labeling agents in the components for PCR. The detector may include, for example, a laser and optics suitable for optical detection of fluorescence from fluorescent labeling agents. The detection module may include one or more photomultiplier tubes. In other examples, other detectors, such as electronic detectors or CCD cameras, may be used. The detection module may further comprise a detector suitable for measuring the temperature of different portions of the disk. The detector may be implemented with a thermistor or an infrared thermometer.

The processing device 720 may include one or more processing units, such as one or more processors. In some examples, the processing device 720 may include a controller, logic circuitry, and/or software for performing functionalities described herein. The processing device 720 may be coupled to one or more memories, input devices, and/or output devices including, but not limited to, disk drives, keyboards, mice, and displays. The processing device may provide control signals to the motor 705, to rotate the disk 400 at selected speeds for selected times. The processing device may provide control signals to the detection module 710, including one or more detectors and/or actuators, to detect signals from the labeling agents or temperature from different regions of the disk 400. The processing device may develop these control signals in accordance with input from an operator and/or in accordance with software including instructions encoded in one or more memories, where the instructions, when executed by one or more processing units, may cause the processing device to output a predetermined sequence of control signals. The processing device 720 may receive electronic signals from the detection module 710 indicative of the detected signal from labeling agents. The processing device 720 may detect a target product and/or calculate a quantity of a target product in a fluid sample based on the signals received from the detection module 710. Accordingly, the processing device 720 may perform calculations. The calculations may be performed in accordance with software including one or more executable instructions stored on a memory causing the processing device to perform the calculations. Results may be stored in memory, communicated over a network, and/or displayed. It is to be understood that the configuration of the processing device 720 and related components is quite flexible, and any of a variety of computing systems may be used including server systems, desktops, laptops, controllers, and the like.

Figure 6:
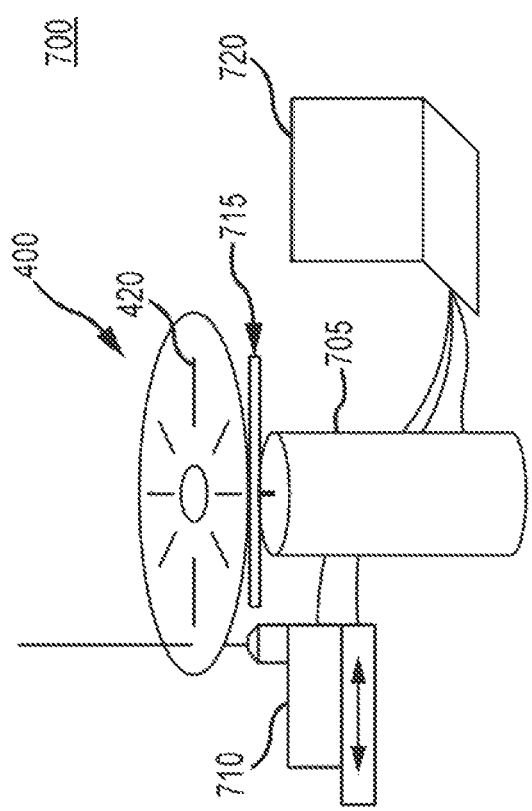
FIG. 6 is a schematic illustration of a system arranged in accordance with embodiments of the present invention.

Accordingly, in some examples the processing device 720 may be configured (e.g. programmed, which may be through the use of executable instructions stored on a computer readable medium) to perform PCR. A user, or another system (e.g. a robotic dispenser), may input a sample into an assay region of the microfluidic disk shown in FIG. 6. The user (or other system) may provide an indication to the processing device 720 that PCR should be implemented. The processing device 720 may provide control signals to implement the method of FIG. 1 in some examples. For example, the processing device 720 may wait a predefined period of time (e.g. an incubation time) before spinning the disk to transport complexes through the immiscible fluid. Optionally, the processing device 720 may provide a control signal to an actuator to disrupt a control layer separating the incubation chamber from the immiscible fluid chamber. For example, the processing device 720 may provide a control signal to a heater to melt a wax control layer between the chambers. In other examples, the processing device 720 may provide a control signal to an actuator positioned to puncture or otherwise break the control layer.

The processing device 720 may provide control signals to spin the disk to transport complexes through the immiscible fluid. The processing device 720 may further provide control signals to spin the disk to transport complexes into the PCR chamber. In some examples, the processing device 720 may provide control signals to melt, puncture, or otherwise disrupt a control layer to create fluid communication between segments of a PCR chamber and/or between the PCR chamber and the immiscible fluid chamber. For example, the processing device 720 may provide a control signal to a heater to melt a wax control layer between the chambers. In other examples, the processing device 720 may provide a control signal to an actuator positioned to puncture or otherwise break the control layer.

The processing device 720 may further provide control signals to a heater and/or cooler to effect thermocycling for performing PCR in the PCR chamber.

In this manner, automated PCR may be conducted by systems and methods described herein. A user (or other system) may apply a sample to a system described herein, indicate that PCR is to be performed, and a processing device, such as the processing device 720 may provide the control signals to spin the disk, heat the disk, and open any relevant control layers in an appropriate sequence to transport bound complexes through an immiscible fluid into a density medium and perform PCR.

From the foregoing it will be appreciated that, although specific embodiments of the invention have been described herein for purposes of illustration, various modifications may be made without deviating from the spirit and scope of the invention.

What is claimed is:

1. A method of conducting an assay, the method comprising:
    incubating nucleic acids, beads, and a lysis buffer to form complexes, individual ones of the complexes comprising a plurality of nucleic acids and a bead;
    transporting the plurality of complexes through an immiscible fluid into a density medium, wherein said density medium contains polymerase chain reaction (PCR) components, and wherein said density medium has a density greater than said immiscible fluid but lower than said complexes; and
    thermocycling the plurality of complexes, density medium, and PCR components to perform PCR on said nucleic acids in the density medium.

2. The method of claim 1, wherein the transporting occurs, at least in part, by centrifugal force.

3. The method of claim 1, further comprising detecting signal from a PCR product on said nucleic acids in said density medium.

4. The method of claim 1, wherein said incubating occurs in an incubation chamber;
    wherein said immiscible fluid is in an immiscible fluid chamber in fluid communication with the incubation chamber, and wherein said immiscible fluid is immiscible with the lysis buffer;
    wherein said PCR components are in a PCR chamber in fluid communication with the immiscible fluid chamber; and
    wherein said PCR occurs in said PCR chamber.

5. The method of claim 4, wherein the incubation chamber and the immiscible fluid chamber are separated by a first control layer, wherein the immiscible fluid chamber and the PCR chamber are separated by a second control layer, said first and second control layers configured to be broken to create the fluid communication between the incubation chamber and the immiscible fluid chamber and the immiscible fluid chamber and the PCR chamber.

6. The method of claim 4, wherein the incubation chamber, immiscible fluid chamber, and PCR chamber are on a microfluidic disk.

7. The method of claim 5, further comprising:
    a. breaking the first control layer between said incubation chamber and said immiscible fluid chamber; and
    b. breaking the second control layer between said immiscible fluid chamber and said PCR chamber.

8. The method of claim 7, wherein the first control layer and the second control layer are broken by heating the first control layer and the second control layer.

9. The method of claim 7, wherein the PCR chamber comprises a first PCR chamber holding freeze dried PCR components and a second PCR chamber containing the density medium, the method further comprising:
    a. breaking a third control layer between the first and second PCR chambers;
    b. combining the contents of the first and second PCR chambers.

10. The method of claim 1, wherein said immiscible fluid has a density greater than that of said lysis buffer but lower than said complexes.

11. The method of claim 1, wherein said bead has a density greater than that of said immiscible fluid.

12. A method of conducting an assay, the method comprising:
    incubating nucleic acids, beads, and a lysis buffer to form complexes in an incubation chamber, individual ones of the complexes comprising a plurality of nucleic acids and a bead;
    transporting the plurality of complexes through an immiscible fluid in an immiscible fluid chamber into a density medium in a polymerase chain reaction (PCR) chamber, wherein said density medium contains PCR components, wherein said density medium has a density greater than said immiscible fluid but lower than said complexes, wherein the immiscible fluid chamber in fluid communication with the incubation chamber, and wherein the PCR chamber is in fluid communication with the immiscible fluid chamber; and
    thermocycling the plurality of complexes, density medium, and PCR components in the PCR chamber to perform PCR on said nucleic acids in the density medium.

13. The method of claim 12, wherein the transporting occurs, at least in part, by centrifugal force.

14. The method of claim 12, further comprising detecting signal from a PCR product on said nucleic acids in said density medium.

15. The method of claim 12, wherein the incubation chamber, immiscible fluid chamber, and PCR chamber are on a microfluidic disk.

16. The method of claim 12, wherein the incubation chamber and the immiscible fluid chamber are separated by a first control layer, wherein the immiscible fluid chamber and the PCR chamber are separated by a second control layer, said first and second control layers configured to be broken to create the fluid communication between the incubation chamber and the immiscible fluid chamber and the immiscible fluid chamber and the PCR chamber.

17. The method of claim 16, further comprising:
    a. breaking the first control layer between said incubation chamber and said immiscible fluid chamber; and
    b. breaking the second control layer between said immiscible fluid chamber and said PCR chamber.

18. The method of claim 17, wherein the first and the second control layers are broken by heating the first and the second control layers.

19. The method of claim 17, wherein the PCR chamber comprises a first PCR chamber holding freeze dried PCR components and a second PCR chamber containing the density medium, the method further comprising:
    a. breaking a third control layer between the first and second PCR chambers;
    b. combining the contents of the first and second PCR chambers.

20. The method of claim 12, wherein said immiscible fluid has a density greater than that of said lysis buffer but lower than said complexes and/or wherein said bead has a density greater than that of said immiscible fluid.

* * * * *